United States Patent
De Faveri et al.

(10) Patent No.: US 8,598,352 B2
(45) Date of Patent: Dec. 3, 2013

(54) PREPARATION OF NALMEFENE HYDROCHLORIDE FROM NALTREXONE

(75) Inventors: Carla De Faveri, Farra di Soligo (IT); Mauro Casarin, Mira (IT); Michele Brusegan, Camponogara (IT)

(73) Assignee: H. Lundbeck A/S, Valby (DK)

( * ) Notice: Subject to any disclaimer, the term of this patent is extended or adjusted under 35 U.S.C. 154(b) by 179 days.

(21) Appl. No.: 13/321,597

(22) PCT Filed: May 21, 2010

(86) PCT No.: PCT/DK2010/050110
§ 371 (c)(1),
(2), (4) Date: Jan. 25, 2012

(87) PCT Pub. No.: WO2010/136039
PCT Pub. Date: Dec. 2, 2010

(65) Prior Publication Data
US 2012/0123123 A1    May 17, 2012

Related U.S. Application Data

(60) Provisional application No. 61/181,022, filed on May 26, 2009.

(30) Foreign Application Priority Data

May 25, 2009 (DK) .................................. 2009 00650

(51) Int. Cl.
*C07D 489/08* (2006.01)
*C07D 489/02* (2006.01)

(52) U.S. Cl.
USPC .............................................. 546/44; 546/45

(58) Field of Classification Search
USPC .................................................... 546/44, 45
See application file for complete search history.

(56) References Cited

U.S. PATENT DOCUMENTS

| | | | |
|---|---|---|---|
| 4,535,157 A | 8/1985 | Meltzer et al. | |
| 4,751,307 A | 6/1988 | White | |

FOREIGN PATENT DOCUMENTS

| | | |
|---|---|---|
| EP | 0039066 A2 | 4/1981 |
| EP | 00352025 A2 | 1/1990 |
| WO | WO 2007/110761 | 10/2007 |

OTHER PUBLICATIONS

Hinkley et al., Feb. 10, 2005, Synthesis of a Caryophyllene Isoprenologue, a potential Diterpene Natural Product, Tetrahedron 61, pp. 3671-3680.
J.M Aizapurua, Science of Synthesis, 4 (2001), p. 595.
Wittig et al., Jul. 10, 1954, "Über Triphenyl-phosphin-methylene als olefinbildende Reagenzien I", Chemische Berichte 87: 1318.
Aycock, D.F., 2007, Solvent Applications of 2 Methyltetrahydrofuran in Organometallc and Biphasic Reactions, Organic Process Research & Development, 11:156-159.
Hahn F. and Fishman J., 1975, Narcotic Antagonists. 4. Carbon-6 Derivatives of N-Substituted Noroxymorphones as Narcotic Antagonists, Journal of Medicinal Chemistry 18(3):259-262.
Dr. Rainer Aul et al., May 2007, A Green Alternative to THF, Manufacturing Chemist, pp. 33-34.
Search Report issued May 5, 2013 in Gulf Cooperation Council Application No. GC 2010-15942 filed May 25, 2010.

*Primary Examiner* — Charanjit Aulakh
(74) *Attorney, Agent, or Firm* — Mary Catherine Di Nunzio

(57) ABSTRACT

Method for producing nalmefene hydrochloride from naltrexone, which method is particular well adapted for large-scale industrial application, and has been found to be efficient, to give a high yield and to afford highly pure nalmefene hydrochloride salt.

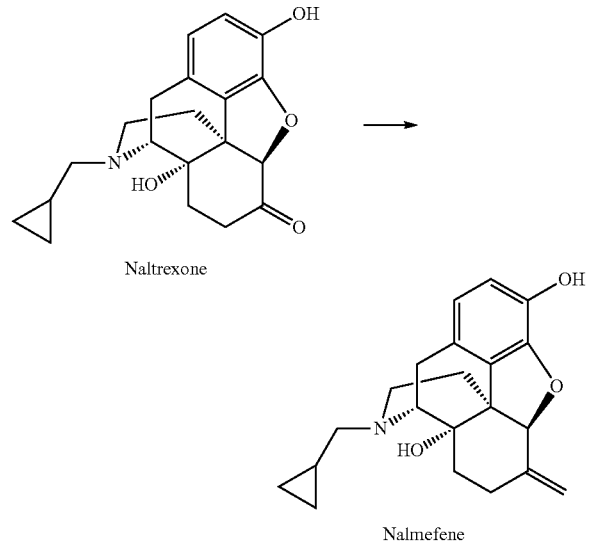

20 Claims, No Drawings

PREPARATION OF NALMEFENE HYDROCHLORIDE FROM NALTREXONE

The present invention relates to an improved method for producing nalmefene hydrochloride [17-(cyclopropylmethyl)-4,5-alpha-epoxy-6-methylenemorphinan-3,14-diol hydrochloride] from naltrexone [17-(cyclopropylmethyl)-4,5-alpha-epoxy-3,14-dihydroxy-morphinan-6-one] by the Wittig reaction. The method disclosed in the present application is particular well adapted for large-scale industrial application, and has been found to be efficient, to give a high yield and to afford highly pure nalmefene hydrochloride salt.

BACKGROUND

Nalmefene is a known opioid receptor antagonist which can inhibit pharmacological effects of both administered opioid agonists and endogenous agonists deriving from the opioid system. The clinical usefulness of nalmefene as antagonist comes from its ability to promptly (and selectively) reverse the effects of these opioid agonists, including the frequently observed depressions in the central nervous system and the respiratory system.

Nalmefene has primarily been developed as the hydrochloride salt for use in the management of alcohol dependency, where it has shown good effect in doses of 10 to 40 mg taken when the patient experiences a craving for alcohol (Karhuvaara et al., *Alcohol. Clin. Exp. Res*., (2007), Vol. 31 No. 7. pp 1179-1187). Additionally, nalmefene has also been investigated for the treatment of other addictions such as pathological gambling and addiction to shopping. In testing the drug in these developmental programs, nalmefene has been used, for example, in the form of parental solution (Revex™).

Nalmefene is an opiate derivative quite similar in structure to the opiate antagonist naltrexone. Advantages of nalmefene compared to naltrexone include longer half-life, greater oral bioavailability and no observed dose-dependent liver toxicity. Nalmefene differs structurally from naltrexone in that the ketone group at the 6-position of naltrexone is replaced by a methylene ($CH_2$) group, which considerably increases binding affinity to the μ-opioid receptor. Nalmefene also has high affinity for the other opioid receptors (κ and δ receptors) and is known as a "universal antagonist" as a result of its ability to block all three receptor types.

Nalmefene can be produced from naltrexone by the Wittig reaction. The Wittig reaction is a well known method within the art for the synthetic preparation of olefins (Georg Wittig, Ulrich Schöllkopf (1954). "*Über Triphenyl-phosphin-methylene als olefinbildende Reagenzien I*". Chemische Berichte 87: 1318), and has been widely used in organic synthesis.

The procedure in the Wittig reaction can be divided into two steps. In the first step, a phosphorus ylide is prepared by treating a suitable phosphonium salt with a base. In the second step the ylide is reacted with a substrate containing a carbonyl group to give the desired alkene.

The preparation of nalmefene by the Wittig reaction has previously been disclosed by Hahn and Fishman (*J. Med. Chem*. 1975, 18, 259-262). In their method, naltrexone is reacted with the ylide methylene triphenylphosphorane, which is prepared by treating methyl triphenylphosphonium bromide with sodium hydride (NaH) in DMSO. An excess of about 60 equivalents of the ylide is employed in the preparation of nalmefene by this procedure.

For industrial application purposes, the method disclosed by Hahn and Fishman has the disadvantage of using a large excess of ylide, such that very large amounts phosphorus by-products have to be removed before nalmefene can be obtained in pure form. Furthermore, the NaH used to prepare the ylide is difficult to handle on an industrial scale as it is highly flammable. The use of NaH in DMSO is also well known by the skilled person to give rise to unwanted runaway reactions. The Wittig reaction procedure described by Hahn and Fishman gives nalmefene in the form of the free base. The free base is finally isolated by chromatography, which may be not ideal for industrial applications.

U.S. Pat. No. 4,535,157 also describes the preparation of nalmefene by use of the Wittig reaction. In the method disclosed therein the preparation of the ylide methylene triphenylphosphorane is carried out by using tetrahydrofuran (THF) as solvent and potassium tert-butoxide (KO-t-Bu) as base. About 3 equivalents of the ylide are employed in the described procedure.

Although the procedure disclosed in U.S. Pat. No. 4,535,157 avoids the use of NaH and a large amount of ylide, the method still has some drawbacks which limit its applicability on an industrial scale. In particular, the use of THF as solvent in a Wittig reaction is disadvantageous because of the water miscibility of THF. During the aqueous work-up much of the end product (nalmefene) may be lost in the aqueous phases unless multiple re-extractions are performed with a solvent which is not miscible with water.

Furthermore, in the method described in U.S. Pat. No. 4,535,157, multiple purification steps are carried out in order to remove phosphine oxide by-products of the Wittig reaction. These purification steps require huge amounts of solvents, which is both uneconomical and labor extensive requiring when running the reaction on an industrial scale. As in the case of the Wittig reaction procedure described by Hahn and Fishman (see above) the Wittig reaction procedure disclosed in U.S. Pat. No. 4,535,157 also yields nalmefene as the free base, such that an additional step is required to prepare the final pharmaceutical salt form, i.e. the hydrochloride, from the isolated nalmefene base.

U.S. Pat. No. 4,751,307 also describes the preparation of nalmefene by use of the Wittig reaction. Disclosed is a method wherein the synthesis is performed using anisole (methoxybenzene) as solvent and KO-t-Bu as base. About 4 equivalents of the ylide methylene triphenylphosphorane were employed in this reaction. The product was isolated by extraction in water at acidic pHs and then precipitating at basic pHs giving nalmefene as base.

Even though the isolation procedure for nalmefene as free base is simplified, it still has some disadvantages. The inventors of the present invention repeated the method disclosed in U.S. Pat. No. 4,751,307 and found that the removal of phosphine oxide by-products was not efficient. These impurities co-precipitate with the nalmefene during basification, yielding a product still contaminated with phosphorus by-products and having, as a consequence, a low chemical purity, as illustrated in example 2 herein.

There is therefore a need within the field to improve the method of producing nalmefene by the Wittig reaction. In particular, there is a need for a method that is readily applicable on a large industrial scale and which avoids the use of water-miscible solvents, such as THF, in the Wittig reaction, and permits easy isolation of nalmefene in a pure form suitable for its transformation to the final pharmaceutical salt form.

The inventors of the present invention have met this goal by developing an improved method for the preparation of nalmefene which is applicable on an industrial scale and results in a highly pure nalmefene as the hydrochloride salt.

SUMMARY OF THE INVENTION

The present invention relates to a method for preparing nalmefene from naltrexone in a Wittig reaction wherein 2-methyltetrahydrofuran (MTHF) is used both in the formation of a phosphorus ylide and in the subsequent reaction between the ylide and naltrexone.

In a further aspect, the invention also relates to a pharmaceutical composition comprising the nalmefene hydrochloride obtained by the method described herein.

DETAILED DESCRIPTION OF THE INVENTION

The present invention relates to an improved method for producing 17-(cyclopropylmethyl)-4,5-alpha-epoxy-6-methylenemorphinan-3,14-diol hydrochloride (nalmefene hydrochloride) from naltrexone [17-(cyclopropylmethyl)-4,5-alpha-epoxy-3,14-dihydroxy-morphinan-6-one].

The inventors of the present invention found that using 2-methyltetrahydrofuran (MTHF) as solvent leads to a highly efficient Wittig process for the preparation of nalmefene. In fact, the use of MTHF in the Wittig reaction not only leads to an efficient reaction, but due to the inherent characteristic of MTHF it makes the isolation of the formed product easier. The whole process and subsequent isolation of the final product in the desired pharmaceutical salt form and purity can be carried out in a one-step procedure without isolation of the base and preparation of the hydrochloride salt in a subsequent and separate step.

MTHF is a polar, aprotic, cyclic ether solvent with good solvation and solubility properties, but in contrast to e.g. THF, MTHF is only partially miscible with water. MTHF is therefore superior to a solvent like THF because it does not require the addition of other solvents, such as toluene, to provide phase separation after the reaction in order to isolate the final product. Therefore, by using MTHF during the aqueous work-up of the Wittig reaction the loss of product in the water phases is very limited or negligible thus rendering re-extraction of the aqueous phases unnecessary.

In a method according to the present invention the Wittig reaction may be performed by mixing a methyltriphenylphosphonium salt with 2-methyltetrahydrofuran (MTHF) and a suitable base to afford the ylide methylene triphenylphosphorane:

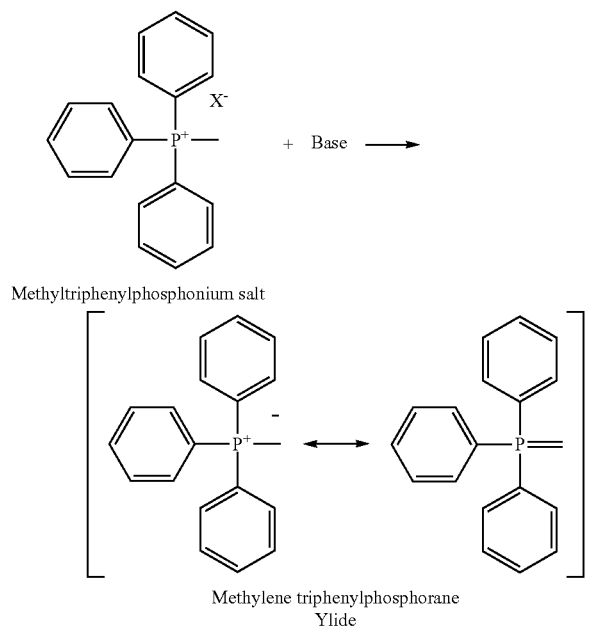

Methyltriphenylphosphonium salt

Methylene triphenylphosphorane
Ylide

The preformed ylide is subsequently reacted 'in situ' with naltrexone to give nalmefene and triphenylphosphine oxide (TPPO):

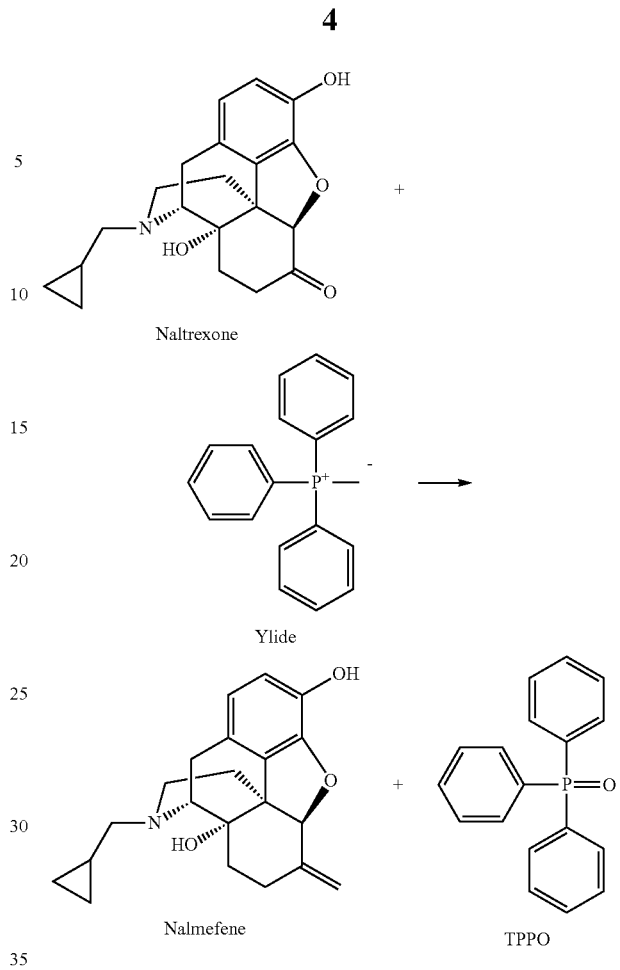

Naltrexone

Ylide

Nalmefene

TPPO

Accordingly, one embodiment of the present invention relates to a method for preparing nalmefene using the basic principles of the Wittig reaction, the method comprising the steps of a) preparing a phosphorus ylide, such as a methylene phosphorus ylide, such as methylene triphenylphosphorane, by mixing a suitable phosphonium salt, such as a methyl triphenyl phosphonium salt, with MTHF and a suitable base, and b) adding a mixture comprising naltrexone and MTHF to the mixture obtained in step a) in order to obtain nalmefene.

It is envisaged that steps a) and b) may be performed simultaneously in the same vessel or step a) and b) may be performed sequentially.

In a preferred embodiment, the phosphonium salt used in step a) is a methyltriphenylphosphonium halide, such as the chloride, bromide or iodide, and more preferably is methyltriphenylphosphonium bromide (MTPPB).

The phosphonium salt, preferably MTPPB, is usually suspended in MTHF in an excess relative to naltrexone added in step b). Typical molar ratio ranges are from about 1:1 to about 4:1, more preferably about 3:1, of methyltriphenylphosphonium salt relative to naltrexone.

The amount of MTHF relative to methyltriphenylphosphonium salt, preferably MTPPB, used in step a) is about (v/w) 1:1 to about 4:1, preferably about 2:1.

The methyltriphenylphosphonium salt is treated with a base, preferably KO-t-Bu, in order to obtain the ylide as a reagent for step b). In a preferred embodiment, the base is used in an equimolar quantity relative to the methyltriphenylphosphonium salt.

Relative to Naltrexone, the molar ratio of the base used in step a) is from about 1:1 to about 4:1, preferably about 3:1.

The resulting mixture obtained in step a) is suitably stirred for at least 1 hour, more preferably for about two hours.

In step b), naltrexone as anhydrous solid or as an anhydrous solution in MTHF is added to the mixture comprising the ylide obtained in a).

In a preferred embodiment, an anhydrous solution of naltrexone in MTHF is added to the pre-formed ylide. The amount (v/w) of MTHF relative to naltrexone may range from about 2:1 to about 6:1, such as about 3:1 to about 5:1, or about 4:1.

The mixture obtained in step b), comprising Naltrexone, is then suitably stirred for at least 1 hour, such as from about 2 to about 16 hours, from about 2 to about 10 hours or from about 2 to about 5 hours, in order to complete the conversion of naltrexone into nalmefene. Typically, it is substantially complete within five hours.

The overall reaction [i.e. step a) and step b)] may be performed at a temperature in the range from about 5 to about 50° C., such as between 20 and 25° C.

Separation of nalmefene from the phosphine oxide by-products (such as TPPO) formed during the Wittig reaction and during the work-up needs to be performed in order to obtain pure nalmefene. The method of the present invention is therefore also advantageous in that it has been especially adapted to:

1) remove efficiently and selectively the phosphorus oxide by-products (TPPO and related compounds); and
2) permit the isolation of the product directly from the reaction mixture and to transform it into the desired pharmaceutical salt form (i.e. nalmefene HCl) in a single step.

Therefore, there is no need to carry out a separate salt formation step (as is often the case in the prior art methods) which results in loss of end product (nalmefene HCl).

Furthermore, the isolation of nalmefene as the hydrochloride salt instead of the free base is convenient from an operational point of view, as the hydrochloride salt is the desired pharmaceutical salt form. It has also been found that the chemical purity is highly improved in the salt formation by the method of the present invention. In fact, the impurities remain selectively dissolved in the mother liquors, thus allowing isolation of the product in a highly pure form.

Since the Wittig reaction and the salt formation steps are combined in the method of the present invention, the yield of nalmefene HCl from naltrexone is excellent.

The invention therefore also relates to a method for isolating nalmefene obtained in step b) above, which method comprise the steps of;

c) (i) mixing an aqueous solution comprising ammonium chloride ($NH_4Cl$) with the mixture obtained in step b), or
  (ii) mixing an acid or a solution containing an acid with the mixture obtained in step b), or
  (iii) mixing a ketone with the mixture obtained in step b), or
  (iv) performing a combination of the above steps (i), (ii) and (iii), and then
  (v) optionally diluting with water,
d) separating the organic phase obtained in step c),
e) optionally washing the mixture obtained in d) with water and separating the organic phase,
f) concentrating the organic phase obtained in step d) or e) under vacuum to remove volatiles,
g) diluting the residue obtained in step f) with one or more appropriate organic solvents,
h) adding hydrogen chloride (HCl) to the mixture obtained in step g),
i) isolating the resulting solid,
j) optionally, re-slurrying the solid obtained in step i) in one or more appropriate solvents and isolating the solid, and
k) optionally drying the final solid.

In one embodiment of step c), the reaction mixture obtained in step b) is suitably quenched with a solution of ammonium chloride ($NH_4Cl$) while maintaining the temperature below 30° C. Usually, ammonium chloride is used in equimolar quantity relative to the base used in step a).

In one further embodiment of step c), the reaction mixture obtained in step (b) is treated with an acid. Said acid is preferably glacial acetic acid or a solution of glacial acetic acid in MTHF. In one embodiment said acid is glacial acetic acid. In another embodiment said acid is glacial acetic acid in MTHF.

In another embodiment of step c), the reaction mixture obtained in step (b) is treated with a ketone. Said ketone is preferably acetone.

In a further embodiment the reaction mixture obtained in step (b) is processed performing a combination of steps c) (i), c) (ii) and c) (iii).

The mixture may optionally be further diluted with water to completely dissolve the salts (step c) (v)). The resultant mixture then contains two phases, an organic and an aqueous phase, which may be separated (step d). The isolated organic phase may then again optionally be washed with water and separated (step e).

The separated organic phase (step d or e) contains nalmefene and may be concentrated under vacuum to leave a residue (step f).

The final residue obtained in step f) may be dissolved in a suitable organic solvent (step g). A suitable solvent is one which can keep triphenylphosphine oxide and related phosphine oxides in solution, which permits the preparation of the hydrochloride salt of nalmefene, as well as its precipitation. Suitable solvents include halogenated hydrocarbons, alcohols, ethers, ketones, esters and aromatic hydrocarbons. Preferred solvents are acetone, ethyl acetate, MTHF, 2-propanol, toluene or dichloromethane, or a combination thereof. Preferably, dichloromethane is used.

The organic solution is then treated with hydrogen chloride (HCl) to precipitate nalmefene as the hydrochloride salt (step h). The acid can be added as a gas or as concentrated aqueous solution of hydrochloric acid. When using hydrochloric acid, the concentration of HCl is usually from about 30 to about 37% in water, more preferably about 37% in water.

The hydrochloride salt formation is carried out at a temperature in the range of from about 0 to about 40° C., preferably 20-30° C., under vigorous stirring.

The product crystallises out during the addition of the acid. Phosphine oxides might be entrapped in the crystalline product, and therefore it is convenient to maintain the suspension under stirring for at least 1 hour, such as between about 1 hour and about 5 hours, or between about 1 hour and about 3 hours.

The resulting solid may then be isolated e.g. by filtering off and washing the product (step i) with appropriate solvents, such as halogenated hydrocarbons, alcohols, ethers, ketones, esters or aromatic hydrocarbons. Preferred solvents are acetone, ethyl acetate, MTHF, 2-propanol, toluene or dichloromethane or a combination thereof. Preferably, dichloromethane is used.

If necessary the product may be re-slurried (step j) in an appropriate solvent chosen from the solvents listed above in order to further remove the phosphine oxide by-products, and the nalmefene hydrochloride may then be filtered off and washed with appropriate solvents, as mentioned above. A preferred solvent for this last step is dichloromethane. The product may finally be dried e.g. under vacuum.

Nalmefene HCl obtained according to the method of the present invention can be transformed into a form more suitable for pharmaceutical formulation, such as the dihydrate. Nalmefene HCl prepared by the above-described Wittig process may be transformed into nalmefene HCl dihydrate by recrystallisation from aqueous solution as described in Example 5 herein.

A further aspect of the present invention thus relates to a method for obtaining nalmefene HCl dihydrate, which method may comprise the steps of:
(1) mixing nalmefene hydrochloride, obtained in step i, j or k as described above, and water,
(2) heating the mixture to obtain a substantially homogenous solution,
(3) optionally removing volatiles from the solution obtained in step (2),
(4) cooling the solution obtained in step (2) or (3) and then seeding the solution with nalmefene HCl, and
(5) isolating the resulting solid.

In the present invention, the term "substantially homogenous solution" is intended to mean a liquid mixture free of visible undissolved material.

The amount of aqueous solution, such as water, which is used in step 1) may range from about 0.9 ml to about 4 ml water per gram nalmefene hydrochloride, such as from about 1 ml to about 2 ml water per gram nalmefene hydrochloride, or about 1.5 ml water per gram nalmefene hydrochloride.

The suspension may be heated until a substantially homogenous solution is obtained. The heating in step 2) may be performed to obtain a temperature of from about 50° C. to about 100° C., such as from about 50° C. to about 90° C., or from about 70° C. to about 85° C.

Partial vacuum may then be applied to remove traces of organic volatiles, if present, in step 3).

The solution obtained from either step 2) or step 3) may optionally be filtered (e.g. through a 0.65 µm cartridge) to remove foreign matter before proceeding to step 4).

In step 4), the solution may be cooled to a temperature between 40° C. to 60° C., such as between 40° C. and about 50° C., and seeded with Nalmefene HCl. Preferably Nalmefene HCl dihydrate is used as seeding material.

In the present invention, the term "seeding" is intended to mean the addition of a small amount of crystalline solid in order to initiate the precipitation of the product.

The amount of seed crystals added in step 4) may be from about 1/2000 (w/w) of seed crystal of nalmefene HCl/nalmefene HCl added in step 1), such as from about 1/1000 (w/w) of seed crystal or 1/200 of seed crystal of Nalmefene HCl/Nalmefene HCl added in step 1).

Rapid cooling and vigorous stirring prevent the crystals that are already formed from growing further, and help to achieve a product with a well defined, narrow size range and relatively small particle size. The cooling from seeding temperature to isolation temperature may be performed over a period of a few hours, preferably within 1 hour. The seeded mixture obtained in step 4) may thus suitably be subjected to a fast cooling procedure which comprises the steps of:
(4') further cooling of the mixture to a temperature of about 0-5° C. over a time period of about 45 minutes or more, and
(4") maintaining the resulting mixture at a temperature of about 0-5° C. for about 45 minutes or more,
before isolating the formed solid according to step 5).

The solid formed in step 5) may be isolated at a temperature within the range of about 0-20° C., more preferably in the range of 0-5° C., in order to minimize the solubility of the product in water and to increase the yield. The solid may be isolated by filtration and washed with a suitable solvent. Suitable solvents for washing include water, mixtures of water and organic solvents, and pure organic solvents. Preferably, water is used, and in a further embodiment pre-cooled water is preferred. When organic solvents are used, Class 2 or 3 solvents are preferred, more particularly acetone.

The product may suitably be dried under vacuum at a temperature below 40° C., more preferably at a temperature in the range 25-35° C.

The product obtained will typically be at least 98% chemically pure, such as at least 99% chemically pure, or at least 99.5% chemically pure. The term chemically pure in this context has its normal meaning within the art, and chemical purity may be determined by e.g. HPLC.

The present invention also relates to a pharmaceutical composition comprising nalmefene hydrochloride obtained by the present method. The pharmaceutical composition may further comprise at least one pharmaceutically acceptable excipient, carrier and/or diluent, and may be in a solid dosage form, such as a tablet, for oral administration.

Methods for the preparation of solid pharmaceutical preparations are well known in the art. See, e.g., Remington: The Science and Practice of Pharmacy, 21st ed., Lippincott Williams & Wilkins (2005). Solid preparations, such as tablets, may be prepared by mixing the active ingredients with an ordinary carrier, such as an adjuvant and/or diluent, and subsequently compressing the mixture in a tabletting machine. Non-limiting examples of adjuvants and/or diluents include: corn starch, lactose, talcum, magnesium stearate, gelatine, lactose, gums, and the like. Any other appropriate adjuvant or additive such as colourings, aroma, and preservatives may also be used provided that they are compatible with the active ingredients. The pharmaceutical compositions of the invention thus typically comprise an effective amount of Nalmefene HCl and one or more pharmaceutically acceptable carriers.

Nalmefene HCL obtained according to the present invention may be administered in any suitable way, e.g. orally or parenterally, and it may be presented in any suitable form for such administration, e.g., in the form of tablets, capsules, powders, syrups or solutions or dispersions for injection. In one embodiment, the pharmaceutical composition will comprise nalmefene in a therapeutically effective amount. The term "therapeutically effective amount" refers to the amount/dose of a compound or pharmaceutical composition that is sufficient to produce an effective response (i.e., a biological or medical response of a tissue, system, animal or human sought by a researcher, veterinarian, medical doctor or other clinician) upon administration to a patient. The "therapeutically effective amount" will vary depending on, inter alia, the disease and its severity, and on the age, weight, physical condition and responsiveness of the patient to be treated. Furthermore, the "therapeutically effective amount" may vary if the compound of the invention is combined with one or more compounds: In such a case the amount of a given compound might be lower, such as a sub-effective amount.

Preferably, the amount of Nalmefene HCl in a pharmaceutical composition in unit dosage form is amount from about 10 mg to about 100 mg, such as from about 10 mg to about 60 mg, e.g. from about 10 mg to about 40 mg, or about 20 mg.

In particular, it is envisaged that a pharmaceutical composition of the present invention may be used for treating alcohol dependency. In another embodiment, a composition comprising nalmefene HCl obtained by the present method may be used for the manufacture of a medicament for treatment of alcohol dependency.

In another embodiment, the invention relates to a method for treating alcohol dependency, comprising administering a therapeutically effective amount of nalmefene HCl obtained by the present method, or a pharmaceutical composition thereof, to a patient in the need thereof.

The term "alcohol dependency" is a commonly known term for a skilled person. In the revised 4th edition of the Diagnostic and Statistical Manual of Mental Disorders (DSM-IVTR) (*Diagnostic and Statistical Manual of Mental Disorders*, 4th edition text revision, American Psychiatric Publishing, 2000), the term "alcohol dependency" is defined as the presence of three or more of the seven areas of life impairment related to alcohol in the same 12-month period. These impairments include tolerance, evidence of a withdrawal syndrome when alcohol is discontinued or intake is decreased, potential interference with life functioning associated with spending a great deal of time using alcohol, and returning to use despite evidence of physical or psychological problems.

EXAMPLES

Example 1

Methyltriphenylphosphonium bromide (MTPPB, 25.8 Kg) was suspended in 2-methyltetrahydrofuran (MTHF, 56 liters). Keeping the temperature in the range 20-25° C., KO-t-Bu (8.8 kg) was charged in portions under inert atmosphere in one hour. The suspension turned yellow and was stirred further for two hours. An anhydrous solution of naltrexone (8.0 Kg) in MTHF (32 liters) was then added over a period of one hour at 20-25° C. The suspension was maintained under stirring for a few hours to complete the reaction. The mixture was then treated with a solution of ammonium chloride (4.2 Kg) in water (30.4 liters) and then further diluted with water (30.4 liters). The phases were separated, the lower aqueous phase was discarded and the organic phase was washed twice with water (16 liters). The organic phase was concentrated to residue under vacuum and then diluted with dichloromethane (40 liters) to give a clear solution. Concentrated aqueous hydrochloric acid (HCl 37%, 2 liters) was added over one hour at 20-25° C. The suspension was stirred for at least three hours at the same temperature, and then filtered and washed with dichloromethane (8 liters) and then with acetone (16 liters). The solid was then re-suspended in dichloromethane (32 liters) at 20-25° C. for a few hours and then filtered and washed with dichloromethane (16 liters), affording 9.20 Kg of nalmefene hydrochloride, corresponding to 7.76 kg of nalmefene hydrochloride (99.7% pure by HPLC). Molar yield 89%.

| HPLC Chromatographic conditions | |
| --- | --- |
| Column: | Zorbax Eclipse XDB C-18, 5 µm, 150 × 4.6 mm or equivalent |
| Mobile Phase A: | Acetonitrile/Buffer pH = 2.3 10/90 |
| Mobile Phase B: | Acetonitrile/Buffer pH = 2.3 45/55 |
| Buffer: | Dissolve 1.1 g of Sodium Octansulfonate in 1 L of water. Adjust the pH to 2.3 with diluted $H_3PO_4$. |
| Column Temperature: | 35° C. |
| Detector: | UV at 230 nm |
| Flow: | 1.2 ml/min |

| HPLC Chromatographic conditions | | |
| --- | --- | --- |
| Injection volume: | 10 µl | |
| Time of Analysis: | 55 minutes | |
| Time (min) | Mobile Phase A Acetonitrile/Buffer 10/90 | Mobile PhaseB Acetonitrile/Buffer 45/55 |
| 0 | 100 | 0 |
| 45 | 0 | 100 |
| 47 | 100 | 0 |
| 55 | 100 | 0 |

Example 2

The procedure described in U.S. Pat. No. 4,751,307 was repeated, starting from 10 g of naltrexone and yielding 8.5 g of nalmefene. The isolated product showed the presence of phosphine oxides by-products above 15% molar as judged by $^1$HNMR.

Example 3

Methyltriphenylphosphonium bromide (MTPPB, 112.9 g) was suspended in 2-methyltetrahydrofuran (MTHF, 245 ml). Keeping the temperature in the range 20-25° C., KO-t-Bu (38.7 g) was charged in portions under inert atmosphere in one hour. The suspension was stirred for two hours. An anhydrous solution of naltrexone (35 g) in MTHF (144 ml) was then added over a period of one hour at 20-25° C. The suspension was maintained under stirring overnight. The mixture was then treated with a solution of glacial acetic acid (17.7 g) in MTHF. Water was then added and the pH was adjusted to 9-10. The phases were separated, the lower aqueous phase was discarded and the organic phase was washed twice with water. The organic phase was concentrated to residue under vacuum and then diluted with dichloromethane (175 ml) to give a clear solution. Concentrated aqueous hydrochloric acid (HCl 37%, 10.1 g) was added over one hour at 20-25° C. The suspension was stirred and then filtered and washed with dichloromethane and acetone. The product was dried affording 38.1 g of Nalmefene HCl.

Example 4

Example 3 was repeated but the Wittig reaction mixture after olefination completeness was treated with acetone and then with an aqueous solution of ammonium chloride. After phase separation, washings, distillation and dilution with dichloromethane, the product was precipitated as hydrochloride salt using HCl 37%. The solid was filtered and dried affording 37.6 g of Nalmefene HCl.

Example 5

Preparation of Nalmefene HCl dihydrate from Nalmefene HCl

Nalmefene HCl (7.67 Kg, purity 99.37%, assay 93.9%) and water (8.6 liters) were charged into a suitable reactor. The suspension was heated up to 80° C. until the substrate completely dissolved. Vacuum was then applied to remove organic solvents. The resulting solution was filtered through a 0.65 µm cartridge and then diluted with water (2.1 liters) that has been used to rinse the reactor and pipelines. The solution was cooled down to 50° C. and 7 g of Nalmefene HCl dihydrate seeding material was added. The mixture was cooled to 0-5° C. over one hour with vigorous stirring and then maintained under stirring for one additional hour. The solid was filtered of and washed with acetone. The wet product was dried at 25° C. under vacuum to provide 5.4 Kg of Nalmefene HCl dihydrate (purity 99.89%, KF 8.3%, yield 69%).

The invention claimed is:

1. A method for preparing nalmefene from naltrexone in a Wittig reaction wherein 2-methyltetrahydrofuran (MTHF) is used both in the formation of a phosphorous ylide and in the subsequent reaction between said ylide and naltrexone.

2. The method according to claim 1, comprising the steps of
   a) preparing a phosphorus ylide by mixing a methyltriphenylphosphonium salt with MTHF and a suitable base, and
   b) adding a mixture comprising naltrexone and MTHF to the mixture obtained in step a).

3. The method according claim 2, wherein the steps a) and b) are performed simultaneously in the same vessel or step a) and b) are performed sequentially.

4. The method according to claim 2, wherein the methyltriphenyl phosphonium salt is selected among methyltriphenylphosphonium bromide (MTPPB), methyltriphenylphosphonium chloride or methyltriphenylphosphonium iodide.

5. The method according to claim 2, wherein said MTHF and said methyltriphenylphosphonium salt are mixed in an amount (v/w) of about 1:1 to about 4:1 of MTHF relative to said methyltriphenyl phosphonium salt.

6. The method according to claim 2, wherein said base added in step a) is potassium tert-butoxide (KO-t-Bu).

7. The method according to claim 6, wherein said KO-t-Bu is added an equimolar quantity relative to methyltriphenyl phosphonium salt.

8. The method according to claim 2, wherein said mixture obtained in step a) is stirred for at least 1 hour, before step b).

9. The method according to claim 2, wherein said naltrexone used in step b) is added as anhydrous solid or as an anhydrous solution in MTHF.

10. The method according to claim 9, wherein an amount of MTHF relative to naltrexone (v/w) is from about 2:1 to about 6:1.

11. The method according to claim 2, wherein the mixture obtained in step b) is stirred for at least 1 hour.

12. A method for isolating nalmefene obtained in step b) according to claim 2, comprising the steps of
   c) (i) mixing an aqueous solution comprising ammonium chloride ($NH_4Cl$) with the mixture obtained in step b), or
      (ii) mixing an acid or a solution containing an acid with the mixture obtained in step b), or
      (iii) mixing a ketone with the mixture obtained in step b), or
      (iv) performing a combination of the above step steps (i), (ii) and (iii), and then
      (v) optionally diluting with water,
   d) separating the organic phase obtained in step c),
   e) optionally washing the organic phase obtained in c) with water and separating the organic phase,
   f) concentrating the organic phase obtained in step d) or e) under vacuum to remove volatiles,
   g) diluting the residue obtained in step f) in one or more appropriate organic solvents,
   h) adding hydrogen chloride (HCl) to the mixture obtained in step g),
   i) isolating the resulting solid,
   j) optionally, re-slurrying the solid obtained in step i) with one or more appropriate solvents and isolating the solid, and
   k) optionally drying the final solid.

13. The method according to claim 12, wherein said organic solvent used in step g), i) and/or step j) is selected from the group comprising halogenated hydrocarbons, alcohols, ethers, ketones, esters and aromatic hydrocarbons or a combination thereof.

14. The method according to claim 12, wherein said organic solvent in step g), i) and/or step j) is selected from acetone, ethyl acetate, MTHF, 2-propanol, toluene, dichloromethane or a combination thereof.

15. The method according to claim 12, wherein said organic solvent in step g), i) and/or step j) is dichloromethane and/or acetone.

16. The method according to claim 12, wherein hydrogen chloride (HCl) in step h) is added as a gas or as concentrated aqueous solution.

17. The method according to claim 12, wherein the concentration of HCl in step h) is about 30 to about 37% in water.

18. The method according to claim 12, wherein hydrogen chloride (HCl) is added in step h) under vigorous stirring at a temperature comprised in the range from about 0 to about 40° C.

19. The method according to claim 12, wherein said mixture obtained in step h) is stirred for at least 1 hour.

20. The method according to claim 12, wherein the Nalmefene HCl obtained is transformed into Nalmefene HCl dihydrate by re-crystallisation in an aqueous solution.

* * * * *